(12) United States Patent
Laurenzi et al.

(10) Patent No.: US 8,172,129 B1
(45) Date of Patent: May 8, 2012

(54) METHOD FOR TRACKING BREAST MILK IN A NEONATAL CARE FACILITY

(75) Inventors: Larry Laurenzi, Avon, OH (US); Giles A. Manias, Broadview Heights, OH (US)

(73) Assignee: Paragon Data Systems, Inc., Cleveland, OH (US)

( * ) Notice: Subject to any disclaimer, the term of this patent is extended or adjusted under 35 U.S.C. 154(b) by 57 days.

(21) Appl. No.: 12/697,610

(22) Filed: Feb. 1, 2010

Related U.S. Application Data (60) Provisional application No. 61/148,552, filed on Jan. 30, 2009.

(51) Int. Cl.
*G06F 17/00* (2006.01)
*G06K 5/00* (2006.01)
*G06Q 50/00* (2012.01)

(52) U.S. Cl. .............................. 235/375; 705/3; 235/380
(58) Field of Classification Search .................. 235/375, 235/380, 385; 705/3
See application file for complete search history.

(56) References Cited

U.S. PATENT DOCUMENTS

| | | | |
|---|---|---|---|
| 2008/0087726 A1 | 4/2008 | Norman et al. | |
| 2009/0157428 A1* | 6/2009 | Auchinleck | 705/3 |

* cited by examiner

*Primary Examiner* — Jamara Franklin
(74) *Attorney, Agent, or Firm* — Ryan O. White; Taft, Stettinius & Hollister, LLP (57) ABSTRACT

A system and method for tracking breast milk in a neonatal facility using optically-scannable identifiers. The optically-scannable identifiers are affixed to containers and measuring devices containing breast milk. The identifiers are used in the association of the containers and measuring devices with an infant.

18 Claims, 7 Drawing Sheets

METHOD FOR TRACKING BREAST MILK IN A NEONATAL CARE FACILITY

RELATED APPLICATION DATA

This application claims the benefit of U.S. Provisional Patent Application No. 61/148,552 filed Jan. 30, 2009, which is incorporated herein by reference in its entirety.

TECHNICAL FIELD

The present invention relates generally to a system for tracking breast milk, and more particularly to a system for tracking breast milk in a neonatal intensive care setting.

BACKGROUND

An infant that is born in a hospital setting typically leaves the hospital after a short stay in a maternity ward. However, if the infant is born prematurely or with health difficulties, the infant may need to be kept in a neonatal intensive care unit (NICU) for an extended amount of time. In such a situation, the mother is often unable to breast feed the infant herself because of the need to carefully monitor the amount of milk that is fed to the infant.

Traditionally, an infant kept in the NICU is fed using breast milk that has been provided by the mother to the NICU. More particularly, the mother expresses breast milk into a container and provides the container to the NICU. A nurse within the NICU subsequently carries the container to the child, fills a measuring device with a measured amount of the breast milk from the container, and attaches the measuring device to the child's feeding tube.

However, this system is purely visual and prone to error in an environment of high activity and stress, such as a NICU. A typical NICU includes multiple infants, and is characterized by the continuous ingress and egress of nurses, technicians, doctors, and mothers. In this environment it is easy for a nurse to inadvertently feed the breast milk to the wrong child.

Systems have been proposed to assist in the monitoring the temperature of expressed breast milk. For example, U.S. Patent Publication No. 2008/0087726 describes a system that utilizes radio frequency identification (RFID) tags in conjunction with a neonatal substrate warming and cooling unit to monitor the temperature of breast milk from the time the breast milk is received by the NICU until it is fed to the infant. The temperature monitoring provided by this system utilizes the RFID tags that can be read when the container is located within a warming oven or refrigeration unit.

SUMMARY OF INVENTION

The present invention provides a system for utilizing optically-scannable identifiers to track breast milk in a NICU. The system associates an infant with a container and measuring device containing the mother's breast milk, which enables the allocation of the mother's breast milk from a container into one or more associated measuring devices in an environment that is removed from the NICU. The present invention reduces the demand on a nurse in the NICU, thereby increasing the likelihood that the infant will receive a correct amount of breast milk from the correct mother, while minimizing the infant's risk of infection or similar adverse effects that could result as a consequence of incorrect feeding.

The present invention provides a method for tracking breast milk in a neonatal facility using optically-scannable identifiers that includes optically scanning an identifier affixed to a container containing breast milk, optically scanning an identifier affixed to a measuring device that contains a measured amount of the breast milk from the container, associating the identifier of the container with the identifier of the measuring device, and associating the identifier of the measuring device to an infant.

Either the identifier of the container or the identifier of the measuring device may be a barcode printed on a label.

The method may further include fortifying the breast milk contained in either the container or the measuring device, and associating either the identifier of the container or the identifier of the measuring device with an indicator that the breast milk has been fortified.

The method may further include associating either the identifier of the container or the identifier of the measuring device with a mother.

The method may further include associating either the identifier of the container or the identifier of the measuring device with a time stamp that represents an age of the breast milk.

The method may further include associating either the identifier of the container or the identifier of the measuring device with a respective inventory of containers or measuring devices.

The method may further include associating the infant to a feeding schedule. The feeding schedule may associate the measuring device from among a plurality of measuring devices to a specific feeding time.

Either the identifier of the container or the identifier of the measuring device may be unique with respect to other containers and measuring devices. Alternatively or additionally, either the identifier of the container or the identifier of the measuring device may be the same as one or more additional containers or measuring devices.

The present invention also provides a method of determining whether breast milk contained within a measuring device may be fed to an infant using an optically-scannable identifier that includes identifying the infant, optically scanning an identifier affixed to the measuring device that contains a measured amount of the breast milk, determining whether the identifier is associated with the infant, and indicating the determination.

The identifier of the measuring device may be a barcode printed on a label.

The method may further include determining whether the breast milk has been fortified.

The method may further include determining an age of the breast milk.

The method may further include determining whether the identifier is associated to a feeding schedule.

The identifier of the measuring device may be unique with respect to other containers and measuring devices. Alternatively, the identifier of the measuring device may be the same as one or more additional measuring devices.

The infant may be fed if the indicated determination is that the measuring device is associated with the infant. The method may further include generating a time stamp as a record of feeding the infant.

Moreover, the present invention provides a system for tracking breast milk in a neonatal facility using optically-scannable identifiers that includes an optical scanner that scans an identifier affixed to a container containing breast milk and an identifier affixed to a measuring device that contains a measured amount of the breast milk from the container, a database, and a computer program stored on a computer readable medium of the computer system for performing the steps of writing identification information of the optically-scanned identifiers to the database, associating the identifier of the container with the identifier of the measuring device, and associating the identifier of the measuring device to an infant.

The foregoing and other features of the invention are hereinafter described in greater detail with reference to the accompanying drawings.

DESCRIPTION

In the description that follows, like components have been given the same reference numerals, regardless of whether they are shown in different embodiments. To illustrate an embodiment(s) of the present invention in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

Figure 1:
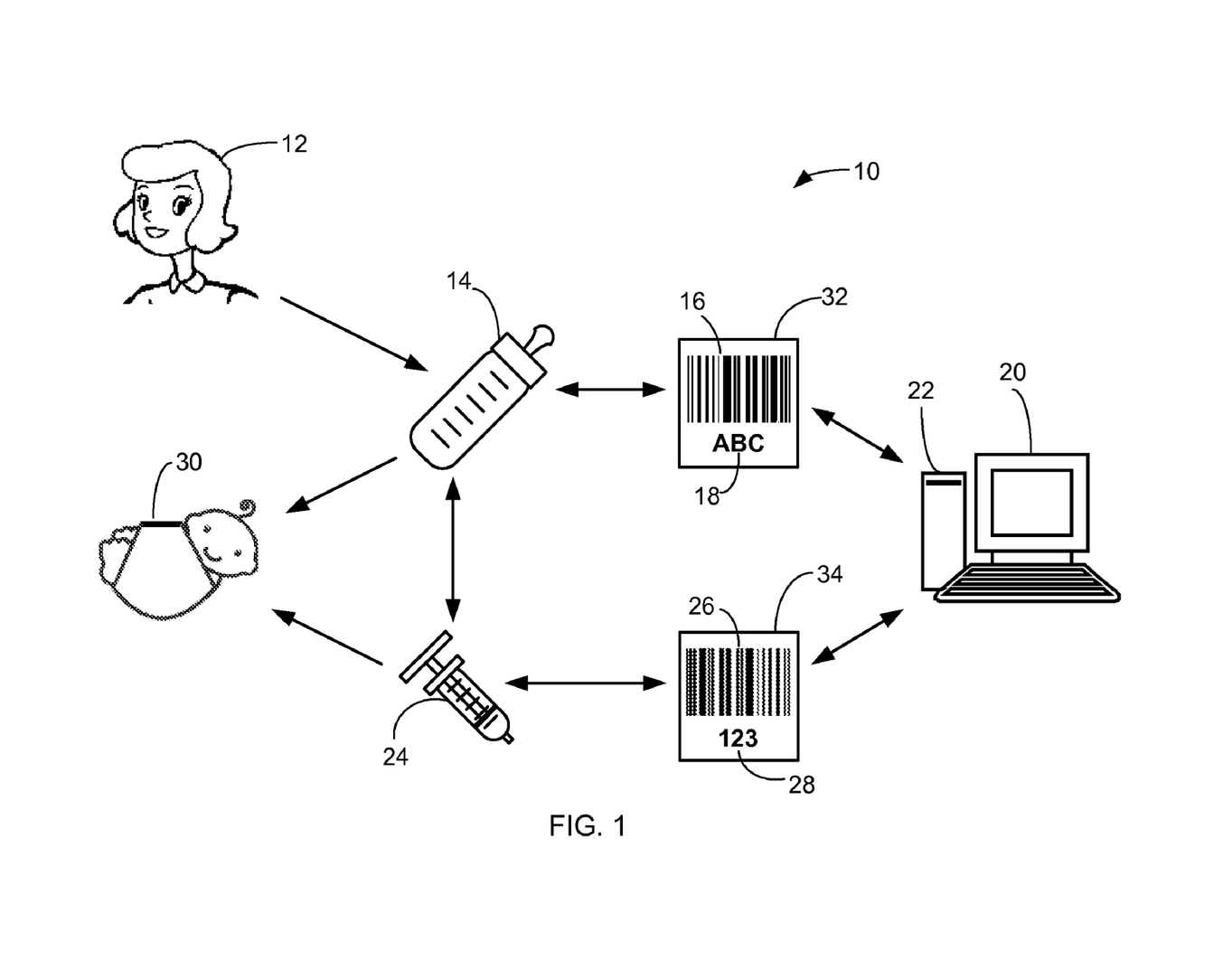
FIG. 1 is a schematic diagram of an exemplary tracking system for tracking the path of breast milk in a NICU in accordance with the invention.

Referring now in detail to the drawings and initially to FIG. 1, a schematic diagram of an exemplary tracking system for tracking the path of breast milk in a NICU in accordance with the invention is shown generally at 10. The tracking system 10 utilizes optically-scannable identifiers such as barcodes 16 and 26, and will herein be described as such. However, it will be appreciated that any suitable optically-scannable identifier may be used in place of barcodes 16 and 26.

In the exemplary tracking system 10, a mother 12 expresses her breast milk into a container, such as a bottle 14. The bottle may have a barcode 16 affixed thereto that represents identification information 18 of the bottle 14. For illustrative purposes, the barcode 18 represents ABC.

The barcode 16 is used to associate the bottle 14 with the mother 12 and the mother's infant 30. In one embodiment, this association may be in place at a time prior to the mother 12 filling the bottle 14. A label 32 may have been previously applied to the bottle 14 that includes the associating barcode 16 and any other written information that pertains to the mother 12 and infant 30. Alternatively, an associated barcode 16 may be pre-printed on the bottle 14. Of course, the association between the bottle 14, mother 12, and infant 30 may be made at a time after the mother 12 fills the bottle 14. As described above, either a label 32 including a barcode 16 or a pre-printed barcode 16 on the bottle 14 may be used to make the association after filling. In such a situation, the label 32 is applied to the bottle 14 after the mother 12 fills it with breast milk and may include additional information such as the date and time that the bottle 14 was filled.

A computer system 20 associates the barcode 16 of the bottle 14 with the infant 30 and the mother 12. Specifically, the computer system 20 may associate the identification information 18 of the barcode 16 with the identity of the infant 30 and the mother 12, and record the information and the association to a database 22 (described in further detail below in relation to FIGS. 4-6).

A measuring device such as a syringe 24 is used to measure a given amount of breast milk from the bottle 14 for feeding the infant 24. The transfer of the breast milk from the bottle 14 to the syringe 24 allows for a desired amount of breast milk 10 to be accurately measured for feeding the infant 30. The syringe may subsequently be coupled to the infant's feeding tube (not shown). Of course, if desired, the bottle 14 may instead be used to feed the infant 30.

The syringe 24 may also include a barcode 26 that represents identification information 28 of the syringe 24. For illustrative purposes, the barcode 28 represents 123. While the barcode 26 of a syringe 24 may represent identification information 28 that is different from the barcode 16 of the bottle 14, the barcode 26 may be applied in the same manner as barcode 16 (e.g., via a label 34 or pre-printed application). The computer system 20 may also associate the barcode 26 to the infant 30 and the mother 12 in the same manner that the barcode 16 is associated. In addition, the computer system 20 may associate the syringe 24 with the bottle 14 via their respective barcodes 16, 26 and identification information 18 and 28.

Figure 2:
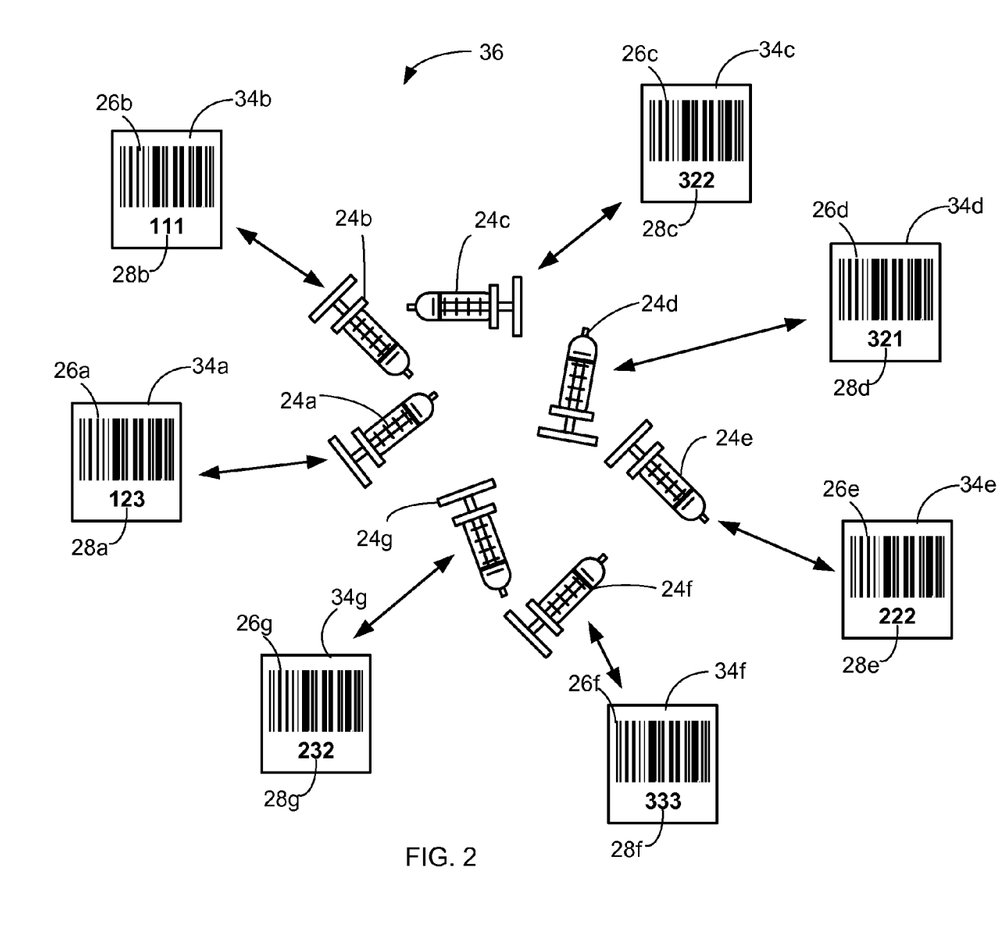
FIG. 2 is a schematic diagram illustrating an exemplary group of syringes having individual identifiers in accordance with the invention.
Figure 3:
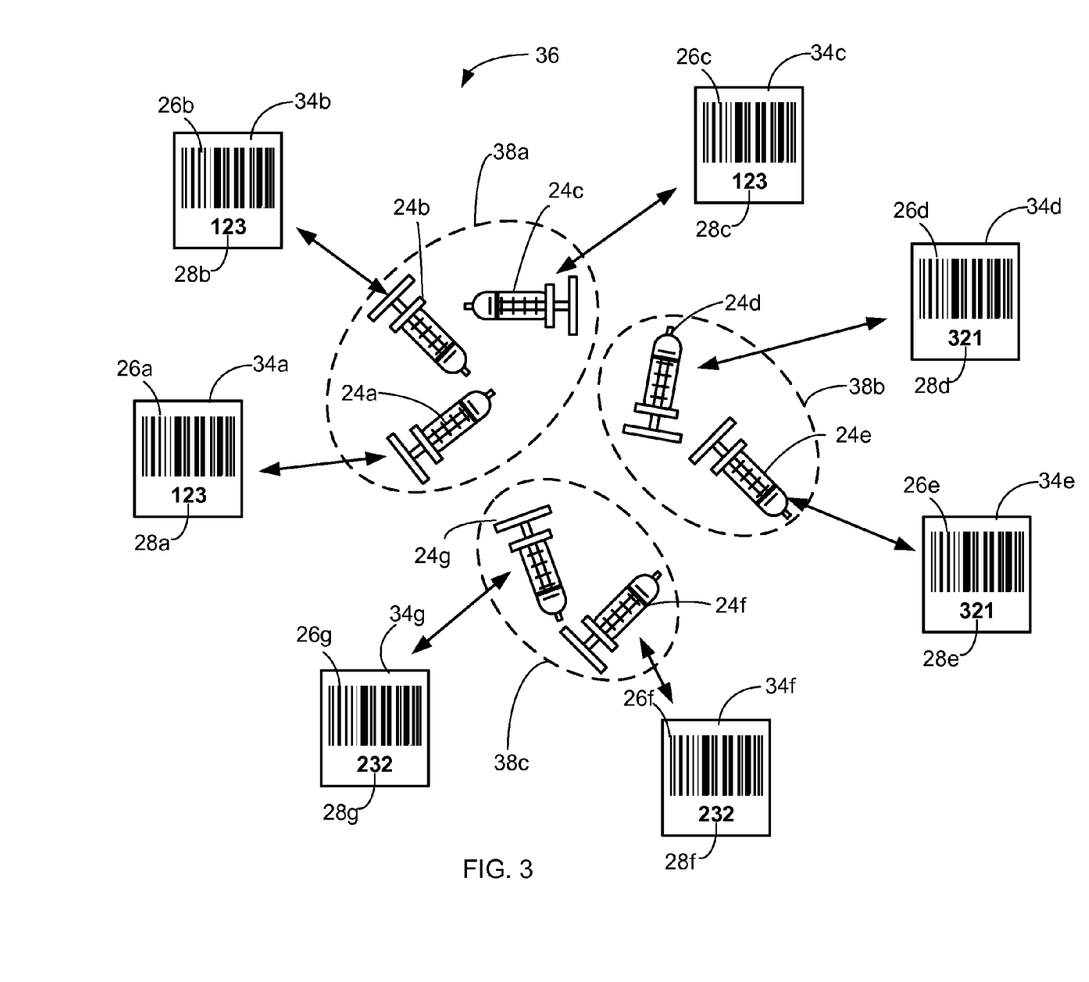
FIG. 3 is a schematic diagram illustrating an exemplary group of syringes having subgroup identifiers in accordance with the invention.

With reference to FIG. 2, a syringe 24 may be selected from among a group of syringes 36. Each syringe 24 may include or be given a barcode 24 that represents unique identification information 28. This allows, for example, for a particular syringe 24 to be to be associated to an infant 30, mother 12, and bottle 14. Alternatively, as illustrated in FIG. 3, a subgroup 38 of syringes 24 may include barcodes 26 that represent common identification information 28. This allows, for example, for a plurality of syringes 24 to be identified as being filled from a particular bottle 14.

The same principles discussed in relation to FIGS. 2 and 3 may be applied to the bottles 14. For example, a particular bottle 14 may be associated to an infant 30, mother 12, and syringe 24. Also, a subgroup of bottles 14 distributed to the mother 12 for filling may include barcodes 16 that represent common identification information 18.

Figure 4:
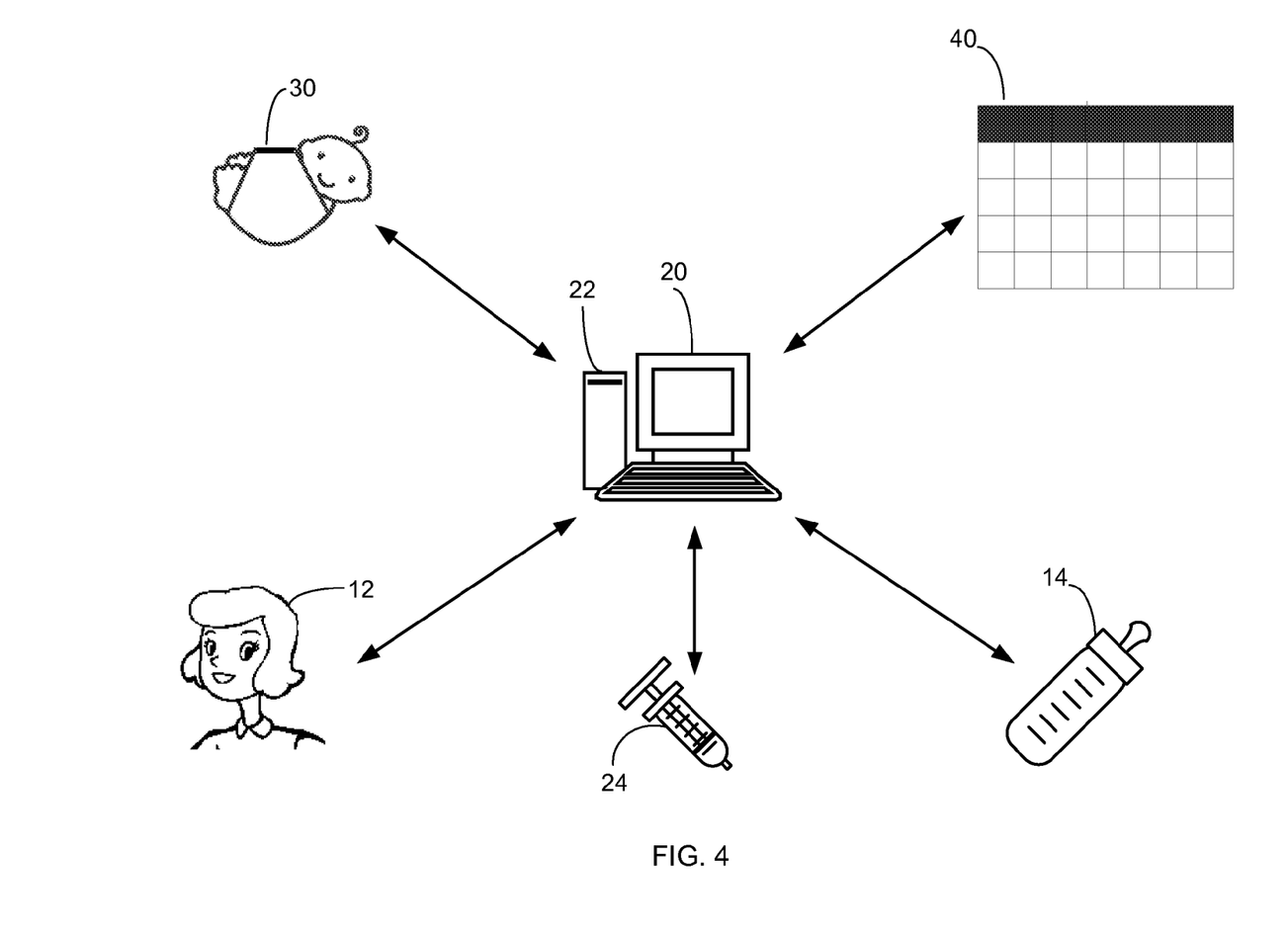
FIG. 4 is a schematic diagram illustrating an exemplary computer system having a database stored thereon for associating an infant, the infant's mother, a bottle of breast milk, a syringe of breast milk, and a feeding schedule in accordance with the invention.

The association of the infant 30, mother 12, bottle 14, and syringe 24 is best described with reference to FIGS. 4 and 5. As discussed above, the computer system associates the identification information 18 and 28 of the respective barcodes 16 and 26 of the bottle 14 and syringe 24 with the infant 30 and the mother 12. This information is stored to the database 22. In one embodiment, one or more computer programs stored on a computer readable medium associated with the computer system 20 perform the above-described association functions, and read and write the information to and from the database 22.

Accordingly, the database 22 of the computer system 20 contains information of the associated infant 30, mother 12, bottle 14, and syringe 24. Thus, if a bottle 14 or syringe 24 is misplaced, it may readily be identified as belonging to the correct infant 30 and mother 12. Even in the instance of a multiple birth, the association of the bottle 14 or syringe 24 to the infant 30 minimizes the likelihood of an accidental feeding mix-up between the siblings. Accordingly, the infant 30 is more likely to be fed as intended.

The database 22 may also include information related to the feeding schedule 40 of the infant. For example, the feeding schedule 40 may include a history of the previous feeding dates, times, and amounts. The feeding schedule 40 may also include future feeding date, time, and amount information. Such future feeding information may be used, for example, to alert a nurse in the NICU to feed a particular syringe 24 to a particular infant 30 (as described in more detail below).

The database may also utilize the barcodes 16, 26 provided on the respective bottles 14 and syringes 24 for purposes other than the association to the infant 30 and mother 12. For example, the barcode 16, 26 may also identify the type of bottle 14 or syringe 24 it is applied to and/or a particular location of the bottle 14 or syringe 24. Such features allow for the monitoring of inventory and frequency of use, implementation of low inventory notices, suggestion of reordering quantities, and/or automatic reordering.

Figure 5:
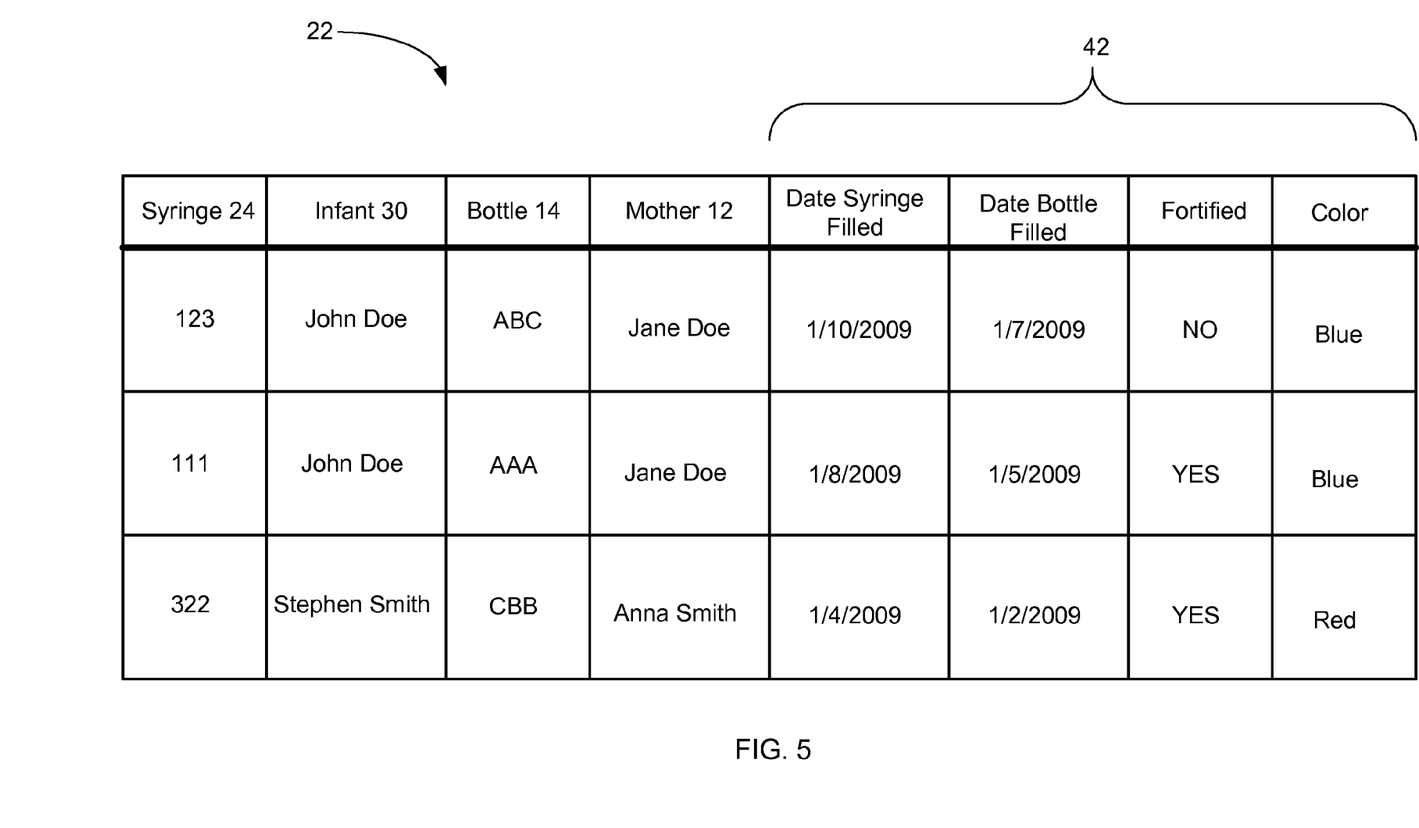
FIG. 5 is a schematic view of an exemplary database in accordance with the invention.

With particular reference to FIG. 5, the database 22 may include at least the above-described fields of information, as well as their association. As illustrated, additional information 42 such as the date that the bottle 14 or syringe 24 was filled may be saved to the database and displayed to a user on the user interface. The information from the database 22 may be displayed, for example, by way of a graphical interface (not shown).

This additional information 42 stored on the database 22 may also include the date and specifics of any fortification performed to the breast milk of a particular bottle 14 and syringe 24. The fortification of a mother's breast milk may be specific to the particular requirements of the infant 30. For example, fortification may include the addition of nutrients, protein, minerals, vitamins, and/or carbohydrates to the breast milk. By indicating the specifics of the fortification, the tracking system 10 may minimize the likelihood of inadvertently feeding the infant 30 non-fortified milk, or feeding the infant 30 over-fortified milk.

In addition to barcodes 16, 26, it is also possible and contemplated to organize the syringes 14 and bottles 26 through color-coding. Adding color-coding to the bottles 14 and syringes 24 of the tracking system 10 may add an additional visual barrier to identify a particular purpose of the fluid in the bottle 14 and syringe 24. This may include using color-coding to distinguish bottles 14 and syringes 24 of milk from a particular mother 12 or for a particular infant 30. The color-coding may also visually distinguish bottles 14 and syringes 24 of milk that require fortification or have been fortified. Such color-coding information may also be recorded to the database 22.

Figure 6:
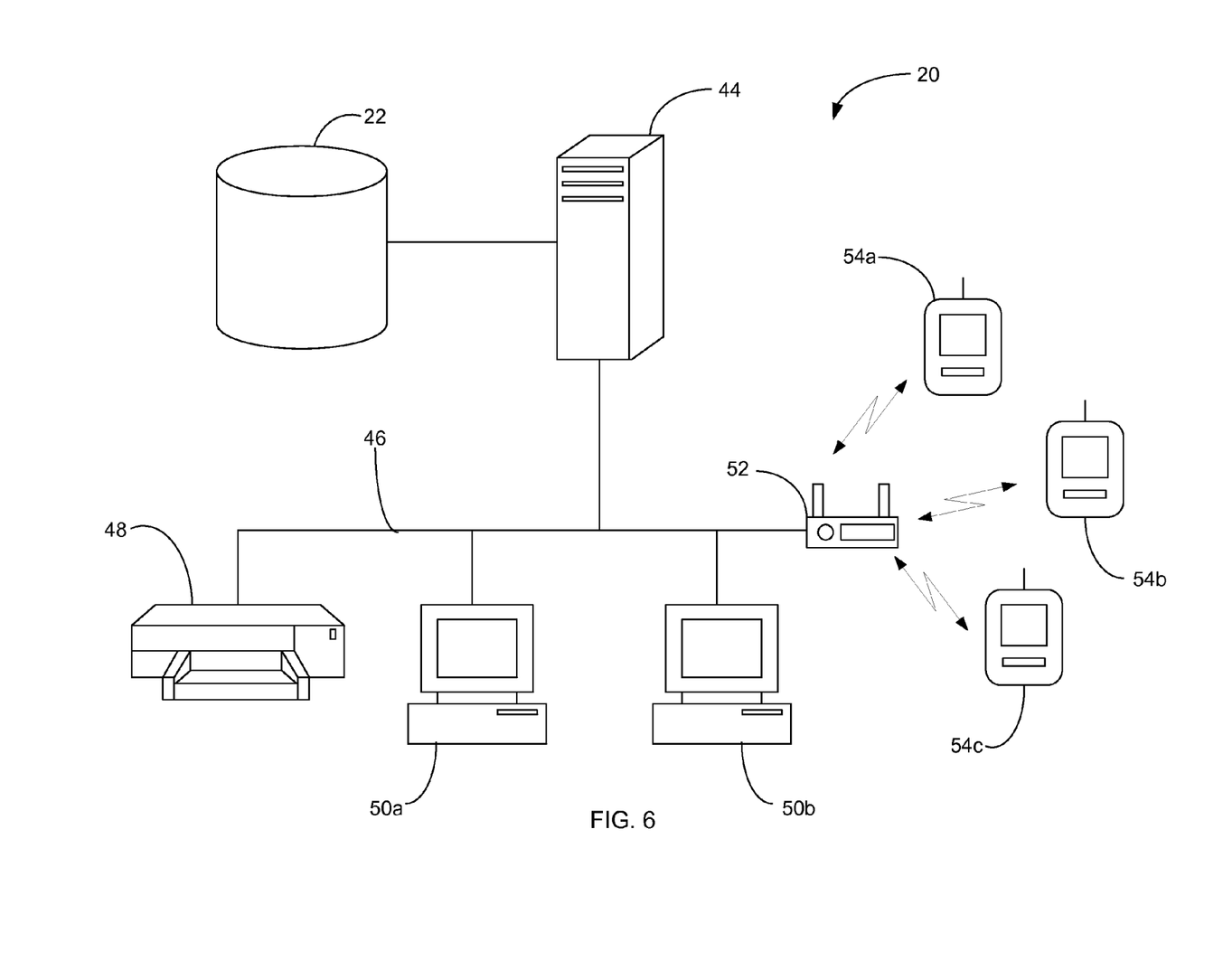
FIG. 6 is a schematic diagram of an exemplary network for implementing the tracking system in accordance with the invention.

With reference to FIG. 6, the computer system 20 may be implemented as a network 46. In this embodiment, the computer system 20 includes the database 22 coupled via a server 44 to one or more workstations 50, printers 48, and handheld devices 54 via the network 46. The workstations 50 may be used to input data and identification information. The printers 75 may be used to print labels 32 and 34 to be used with the bottles 14 and syringes 24.

The one or more handheld devices 54 may be coupled to the network 46 through radio frequency device, such as a wireless router 52. This allows the handheld devices 54 to be easily carried throughout the NICU, and to be located along side the infant 30. These handheld devices 54 may be used to optically scan the barcode 16, 26 of the labels 32, 34 and to indicate whether a bottle 14 or syringe 16 is correctly matched to an infant 30. Furthermore, the handheld devices 54 may be used for data and identification information entry in place of, or in conjunction with, the workstations, and may include integrated label printers.

Figure 7:
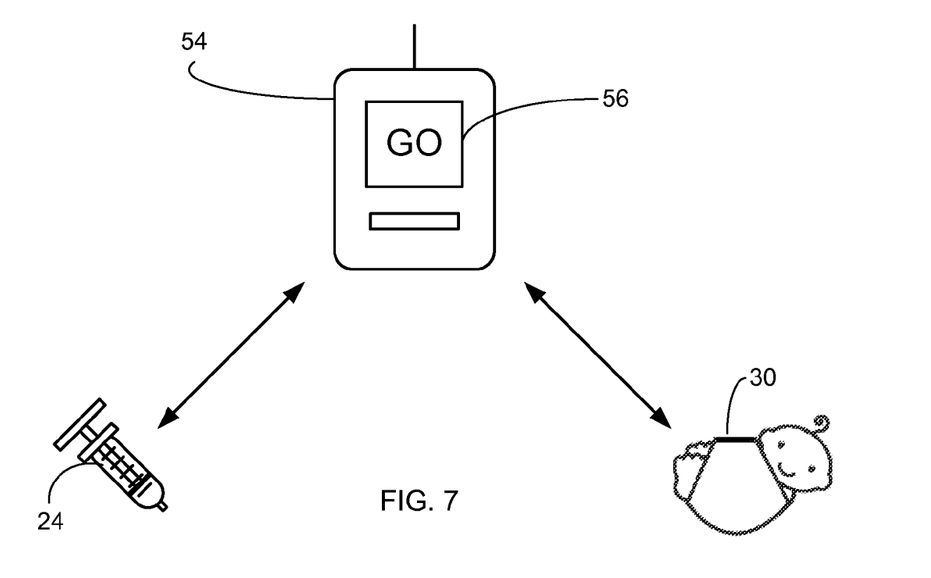
FIG. 7 is a schematic diagram illustrating an exemplary feeding procedure in accordance with the invention.
Figure 8:
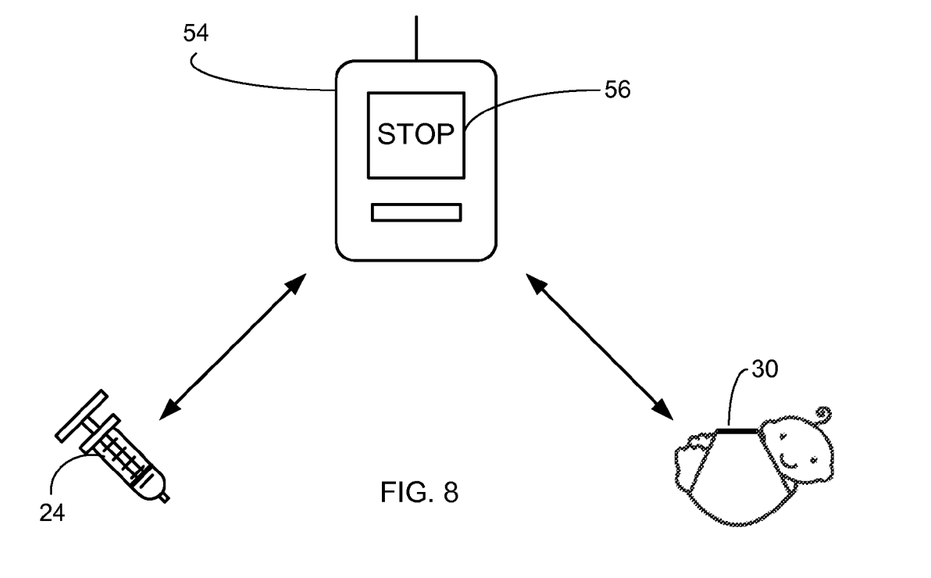
FIG. 8 is a schematic diagram illustrating an exemplary feeding procedure in accordance with the invention.

FIGS. 7 and 8 illustrate an exemplary embodiment wherein a handheld device 54 indicates whether or not to feed a particular infant 30. In this embodiment, the identity of the infant 30 is either associated to a particular handheld device 54, or obtained by the handheld device 54 (e.g., by scanning a barcode associated with the infant or by a nurse manually entering the identity of the infant). The identification information of the syringe 24 is also obtained by the handheld device 54 (e.g., by scanning the barcode affixed to the syringe). If the computer system 20 identifies that the infant 30 and syringe 24 matches the association stored in the database 22, a "GO" indicator is displayed on a display 56 of the handheld device 54 and the infant 30 may be fed with the syringe 24. Alternatively, if a "STOP" indicator is displayed on the display 56, the infant 30 may not be fed with the syringe 24.

It will be understood that parameters other than the association of the infant 30 and the syringe 24 may cause the resultant display of the "STOP" indicator. For example, the infant 30 may have recently been fed, the breast milk may be outdated, the breast milk has not yet been fortified, etc.

It is further contemplated that the handheld devices 54 and/or workstations 50 may be utilized in documenting and maintaining the feeding schedule 40 of the infant 30. For example, time stamps may be generated and saved in the database 22 for purposes of tracking the infant's past feeding times. Furthermore, an alert (e.g., a message displayed on the handheld device and/or workstation) may be provided from the feeding schedule 40 that a particular syringe 24 of breast milk is to be fed to a particular infant 30. Such an alert may be based on such factors as a predetermined feeding schedule, the duration of time since the infant's last feeding, nutritional requirements, etc.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

The invention claimed is:

1. A method for tracking breast milk in a neonatal facility, the method comprising:
   providing a plurality of breast milk feeding and storage instruments, each of the instruments having an identifier affixed thereto;
   associating each of the affixed identifiers with an infant;

scanning one of the affixed identifiers from a first one of the plurality of instruments with an optical scanning device, wherein the first instrument is a container containing breast milk;

scanning another of the affixed identifiers from a second one of the plurality of instruments with the optical scanning device, wherein the second instrument is a feeding device that is configured to feed the infant the breast milk after it the breast milk has been transferred from the first instrument to the second instrument; and recording data obtained from the scanned identifiers in a computer database, the data including identification information unique to the infant.

2. The method of claim 1, wherein the step of scanning one of the affixed identifiers comprises scanning a barcode with the optical scanning device.

3. The method of claim 1, wherein the step of scanning another of the affixed identifiers comprises scanning a barcode with the optical scanning device.

4. The method of claim 1, further comprising fortifying the breast milk contained in either the container or the feeding device.

5. The method of claim 1, wherein the step of associating each of the affixed identifiers with the infant comprises associating at least one identifier affixed to a bottle with the infant.

6. The method of claim 1, wherein the step of associating each of the affixed identifiers with the infant comprises associating at least one identifier affixed to a syringe with the infant.

7. The method of claim 1, further comprising associating each of the affixed identifiers with a mother of the infant.

8. The method of claim 1, further comprising establishing a feeding schedule for the infant from the recorded identification information, the feeding schedule being stored in the computer database.

9. The method of claim 8, further comprising generating an alert relating to the feeding schedule from the computer database to a handheld device or workstation.

10. The method of claim 1, wherein the step of recording data obtained from the scanned identifiers in a computer database comprises using a workstation or handheld device to transmit the identification information over a network to the computer database.

11. The method of claim 10, wherein the workstation or handheld device is coupled to the network through a radio frequency device.

12. A method for tracking breast milk in a neonatal facility, the method comprising:

providing a plurality of breast milk feeding and storage instruments, each of the instruments having a barcode affixed thereto, the barcodes each including identification information unique to an infant and a mother of the infant;

storing breast milk expressed from the mother in a container, the container being one of the plurality of instruments;

scanning a first one of the barcodes that is affixed to the container with an optical scanning device to validate that the identification information is unique to the infant and the mother;

transmitting feeding information over a network to a computer database in response to the scanned first barcode;

transferring the breast milk from the container to a feeding device that is part of the plurality of instruments, the feeding device including a second one of the barcodes affixed thereto;

scanning the second barcode with the optical scanning device to validate that the identification information is unique to the infant and the mother;

transmitting feeding information over a network to a computer database in response to the scanned second barcode; and recording data obtained from the scanned first and second barcodes in the computer database.

13. The method of claim 12, further comprising fortifying the breast milk contained in either the container or the feeding device.

14. The method of claim 12, wherein the step of transferring the breast milk from the container to the feeding device comprises transferring the breast milk to a syringe.

15. The method of claim 12, further comprising establishing a feeding schedule for the infant from the recorded identification information, the feeding schedule being stored in the computer database.

16. The method of claim 15, further comprising generating an alert relating to the feeding schedule from the computer database to a handheld device or workstation.

17. A system for tracking breast milk as the breast milk is transported from a mother to an infant in a neonatal facility, the system including:

an optical scanning device;

a plurality of breast milk feeding and storage instruments, each of the instruments having a barcode including identification information unique to the infant and the mother affixed thereto;

a computer database; and a computer program stored on a computer readable medium for performing the steps of:

processing the identification information from a first one of the barcodes affixed to one of the plurality of instruments after the first one of the barcodes has been scanned with the optical scanning device to validate that the identification information is unique to the infant and the mother;

processing the identification information from a second one of the barcodes affixed to another of the plurality of instruments after the second one of the barcodes has been scanned with the optical scanning device to validate that the identification information is unique to the infant and the mother; and recording the processed identification information from the first and second barcodes in the computer database.

18. The system of claim 17, further comprising a network coupling the optical scanning device to the computer database.

* * * * *

UNITED STATES PATENT AND TRADEMARK OFFICE
CERTIFICATE OF CORRECTION

| | | |
|---|---|---|
| PATENT NO. | : 8,172,129 B1 | Page 1 of 1 |
| APPLICATION NO. | : 12/697610 | |
| DATED | : May 8, 2012 | |
| INVENTOR(S) | : Larry Laurenzi and Giles A. Manias et al. | |

It is certified that error appears in the above-identified patent and that said Letters Patent is hereby corrected as shown below:

Column 7, Claim 1, Line 9, please delete the term "it"

Signed and Sealed this
Twenty-sixth Day of June, 2012

David J. Kappos
*Director of the United States Patent and Trademark Office*